United States Patent [19]

Kupperman et al.

[11] 4,004,597
[45] Jan. 25, 1977

[54] MEANS FOR SUPPORTING A STRIP OR LENGTH OF DENTAL FLOSS IN TENSIONED AND TAUT CONDITION FOR READY USE

[75] Inventors: Sam Kupperman, Chicago; Dennis I. Kupperman, Glenview, both of Ill.

[73] Assignee: RB Toy Development Co., Skokie, Ill.

[22] Filed: July 17, 1975

[21] Appl. No.: 596,736

[52] U.S. Cl. ............................................. 132/84 A
[51] Int. Cl.² ........................................ A45D 44/18
[58] Field of Search ........... 132/92 R, 91, 90, 84 A

[56] References Cited
UNITED STATES PATENTS

| | | | |
|---|---|---|---|
| 2,517,806 | 8/1950 | Streiler | 132/91 |
| 2,577,597 | 12/1951 | Wright et al. | 132/92 R |
| 2,607,358 | 8/1952 | Maas | 132/92 R |
| 3,850,182 | 11/1974 | Clark, Jr. | 132/92 R |

*Primary Examiner*—G.E. McNeill
*Attorney, Agent, or Firm*—Max R. Kraus

[57] ABSTRACT

Means for supporting a strip or length of dental floss in position ready for use. The means comprises a handle with a forked member at the end thereof having a pair of spaced arms and a movable anchoring and locking member supported in an opening in the handle. The strip of dental floss has its terminal ends wound around the stem of the anchoring and locking member and is adapted to lie in the longitudinal grooves in the face of the arms and extend across and between the arms, with the opposite terminal ends of the floss secured to the anchoring and locking member. The movable anchoring and locking member is adapted when moved axially into the opening to tighten the strip of dental floss across the forked arms and lock the opposite ends of the strip against sliding on the stem of the anchoring and locking member during use thereof. The handle may be that of a toothbrush so that the dental floss holder and toothbrush are an integral unit.

1 Claim, 8 Drawing Figures

U.S. Patent  Jan. 25, 1977  4,004,597
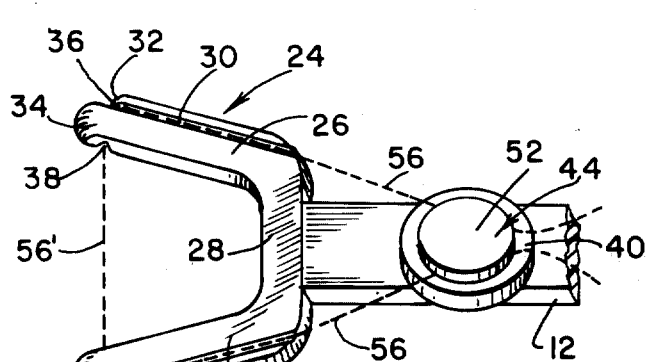
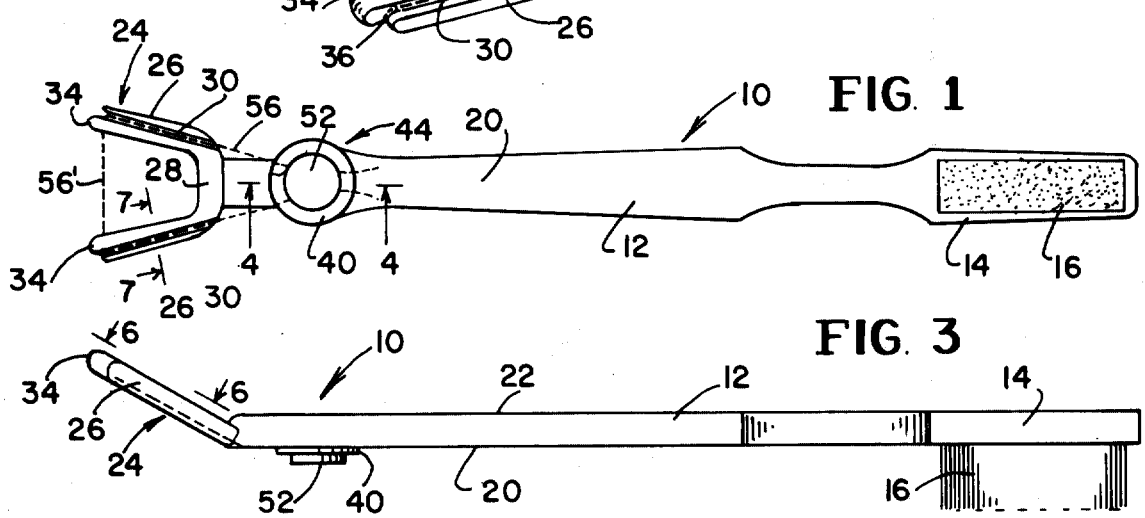
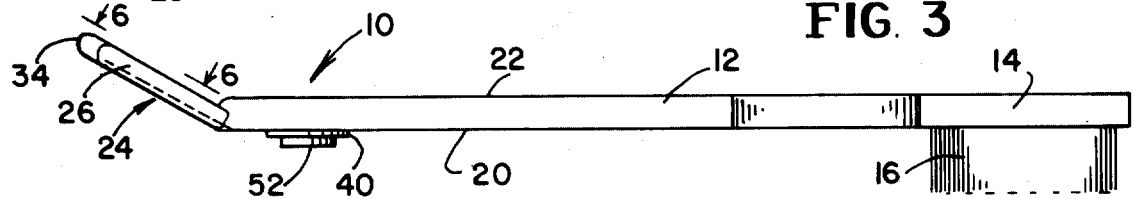
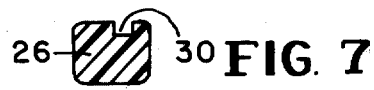
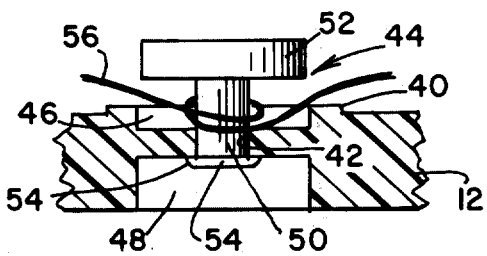
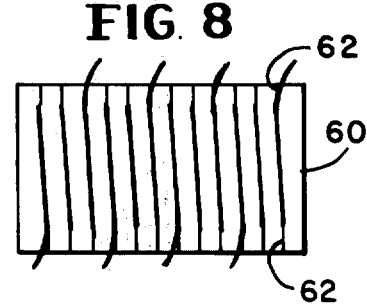
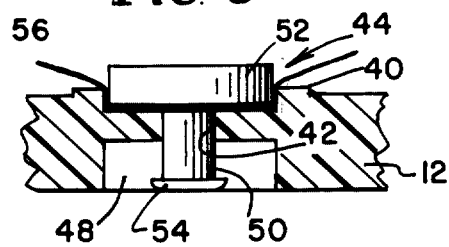
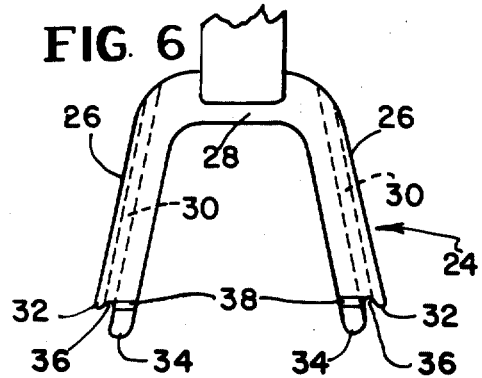

MEANS FOR SUPPORTING A STRIP OR LENGTH OF DENTAL FLOSS IN TENSIONED AND TAUT CONDITION FOR READY USE

BRIEF SUMMARY OF THE INVENTION

Various types of devices are on the market for supporting dental floss. Some devices are associated with a toothbrush in which the dental floss is in a continuous rolled length and is unrolled or unwound from the continuous length when positioned for use. However, such devices are expensive and require threading of the dental floss through small openings, particularly where the device has a pair of spaced arms between which the floss is positioned. Other commercial holders in which the dental floss is unrolled do not have spaced arms for supporting the dental floss in use and such devices require that the free end of the floss be held with one hand while holding a toothbrush in the other hand. Another type of commercial structure utilizes strips or lengths of dental floss passing between spaced arms but such devices do not have positive locking means for anchoring and locking the opposite free ends of the floss in a tensioned position and the free ends of the floss loosen while being used and, in addition, it is not an integral part of the toothbrush.

One of the objects of this invention is to provide a structure which can be economically produced and is easy to use in that a strip of definite length of dental floss is supported on a forked member and is readily anchored to a slidable or movable anchoring and locking member which serves to permit the opposite ends of the strip or length of dental floss to be anchored thereto and when the locking member is slid or moved to locking position the strip or length of floss is tightened on the forked member and held in a taut position during use thereof.

Another object of this invention is to provide a device of the foregoing character which includes a toothbrush which is integrally formed with the means for holding the dental floss in a tensioned and taut condition ready for use and in which such a structure may be inexpensively produced.

Another object of this invention is to provide a dental floss holder which permits the user to reach the back teeth in a much easier manner than that heretofore permitted.

BRIEF DESCRIPTION OF THE DRAWINGS

In the drawings:

FIG. 1 is a front plan view of the invention.

FIG. 2 is a fragmentary view as viewed from the front, showing the forked member on the end of the handle and the dental floss anchoring and locking member.

FIG. 3 is a side elevational view of FIG. 1.

FIG. 4 is an enlarged view partly in section taken on line 4—4 of FIG. 1, showing the dental floss anchoring and locking member in unlocked position.

FIG. 5 is a view similar to FIG. 4 but showing the dental floss anchoring and locking member in locked position.

FIG. 6 is an enlarged rear plan view of the forked member taken on line 6—6 of FIG. 3.

FIG. 7 is an enlarged sectional view taken on line 7—7 of FIG. 1; and

FIG. 8 is a view of a holder for holding the separate strips of dental floss.

The device forming this invention is integrated with a toothbrush and is generally indicated at 10 so that a single structure serves both as a toothbrush and as a means for holding dental floss in a stretched and taut condition ready for use. The device 10 includes a handle generally indicated at 12, with a head 14 at one end to which the conventional toothbrush bristles 16 are secured in the conventional manner. A portion of the handle adjacent the brush end and indicated at 18 is of a reduced width. The front side of the handle adjacent the brush end is indicated at 20 and the rear side is indicated at 22.

The opposite end of the handle is shaped to provide a forked member generally indicated at 24 which includes a pair of spaced diverging arms or members 26 connected at their inner ends by an intermediate member 28 to form a generally U-shaped configuration. The forked member 24 is formed as an integral part of the handle 12. The forked member 24 is inclined rearwardly of the handle at an angle of approximately 30°, as best shown in FIG. 3, so that the forked member 24 is offset rearwardly from the longitudinal plane of the handle 12.

Each of the arms or members 26 of the forked member 24 has a longitudinally extending groove 30 on the front side to receive the strung dental floss, as will be subsequently explained. The upper end or top 32 adjacent th outer side of each of the arms terminates short of the upper end or top 34 of the arm so that the longitudinal groove 30 continues around the radius at the top or upper end of the arm to thereby form a notched portion 36 at the top or upper end of each of the arms for receiving the strung dental floss.

A cross or transversely extending groove 38 is formed in the rear side of each of the arms adjacent the top end to receive the floss and hold it in position as it extends between the arms.

The handle 12 adjacent the forked member 24 but spaced therefrom is provided with an annular enlargement or boss 40 which has a transversely extending annular opening 42, best seen in FIGS. 4 and 5, to receive the floss anchoring and locking member generally indicated at 44. The face or front side of the enlargement or boss surrounding the opening 42 has an annular countersunk or recessed portion 46 and the rear side of the enlargement surrounding the opening has an annular countersunk or recessed portion 48 which is deeper than the recess 46 on the front side.

The dental floss anchoring and locking member 44 includes an annular stem 50 having an annular head or button 52 on one end forming the front. The opposite or rear end of the stem has an annular enlargement or annular lip 54. The floss anchoring and locking member 44 is molded of a plastic material such as polyethylene or polypropelene which has a slight resiliency so that the stem 50 can be initially inserted into the opening 42 through the front side of the handle, with the enlarged end or lip 54 compressing to allow insertion. Thereafter the enlarged end or lip 54 will provide a shoulder and will prevent accidental removal of the floss anchoring and locking member. The floss anchoring and locking member is thus movable or slidable in the opening 42, being pressed or pushed inwardly from the front toward the rear to effect the locking and tensioning of the dental floss, as shown in FIG. 5, and pressed or pushed outwardly toward the front to permit the opposite ends of the dental floss strip to be wound around the stem 50, as shown in FIG. 4.

The dental floss 56 is supplied in definite lengths or strips and is attached to the unit in the following manner. The anchoring and locking member 44 is manually pushed to its unlocked position, as shown in FIG. 4, by inserting the finger against the rear end of the stem and into the recessed portion 48 to position the head or button 52 in a spaced relationship from the front of the handle, thereby exposing a portion of the stem 50. One end of the dental floss 56 is wound once around the stem, as in FIG. 4, then is positioned to lie in the longitudinal groove 30 of one of the arms 26 and around the end notch 36, then passed rearwardly in the cross groove 38 and forwardly to extend down over the notch 36 and down the face of the other arm to lie in the longitudinal groove 30. The opposite terminal end of the floss is then also wound once around the stem 50 of the anchoring and locking member 44. The button or head 52 of the locking member 44 is then pushed inwardly toward the handle and the inner portion of the head will move into the recess or countersunk portion 46 on the front of the handle, as in FIG. 5, thereby wedging the opposite wound ends of the floss between the underside of the head 52 and the wall of the annular recess 46. As this is done the dental floss strip 56 is tightened and tensioned and is firmly anchored. The tail or loose ends of the opposite ends of the floss will extend outwardly of the recessed portion 46. The lower end of the stem 50 will be confined within the recessed portion 48 when same is in locked position, as in FIG. 5, so it will not interfere with the use of the dental floss holder when in the mouth.

The pushing in of anchoring and locking member 44 into the opening 42 thus serves a dual function, namely, to tighten or tension the dental floss strip 56 on the forked member 24 and to lock it. By tensioning the strip of floss 56 that portion which extends between the spaced arms, identified as 56', is maintained under sufficient tension and tautness so that when the device is used and the dental floss is inserted between the teeth, as is well understood, the portion 56' of the floss between the arms will be sufficiently tensioned so that it can serve its purpose of removing foodstuff and the like accumulated between the teeth and yet will have enough "give" so as not to injure the gums. The tension on the dental floss is maintained during use of the device by virtue of the structure of the movable locking member 44 in its relationship in a locked position in the recessed portion 46 of the handle.

The strip of dental floss 56 can be used several times and cleaned after each use by letting water run over the portion 56'. After it has served its purpose the floss is removed by pushing against the free end of the stem 50 and pushing the locking member 44 to the position shown in FIG. 4, after which the wound terminal ends of the floss strip are removed from the stem as by pulling on the floss strip. The device is then ready to receive another strip of dental floss to be secured in the manner previously described. The floss locking member 44 when in locked position, as in FIG. 5, and ready for use is in an out-of-the-way position and does not interfere with the user's hand when holding the handle.

The strips or lengths of dental floss 56 may be wound around a card, such as shown in FIG. 8, for ready use. For example, a card 60 having spaced notches or cuts 62 on its opposite side edges has a strip or length of floss wound around the card and retained in a pair of oppositely positioned notches. Twelve or any number of separate strips or lengths of floss can be wound on a single card, each strip retained in a pair of oppositely positioned notches and a strip of floss is removed when desired for attachment to the device, as previously described.

What is claimed is:

1. In combination a handle supporting a toothbrush at one end and means for supporting a precut strip or length of dental floss in position ready for use at the opposite end, said means comprising a forked member at the end of said handle and integrally formed with said handle, said forked member having a pair of spaced arms, with each of said arms having a longitudinal groove on one of the surfaces and a transversely extending groove on the undersurface, a depressable anchoring and locking member supported in an opening in said handle adjacent said forked member, said handle having a recess around said opening, said depressable anchoring and locking member having a head and a stem with the stem extending into said opening, a precut strip of dental floss having one end adapted to be manually wound around the stem of said anchoring and locking member and extending into the longitudinal groove of one arm and the groove on the undersurface and across to the other arm and extending into the transverse groove and longitudinal groove of said other arm, with the opposite end of said strip of dental floss adapted to be manually wound around the stem of said anchoring and locking member, said depressable anchoring and locking member adapted when moved axially into said opening to move said head into said recess and said stem further into said opening to tighten said strip of dental floss across the forked arms and lock the opposite ends of the strip against sliding on said anchoring and locking member, said stem having means to prevent removal of said stem from said handle, said forked member inclined at an angle of approximately 30° with respect to the longitudinal plane of the handle.

* * * * *